United States Patent [19]

Oakes et al.

[11] Patent Number: 5,236,616

[45] Date of Patent: Aug. 17, 1993

[54] BLEACHING COMPOSITION

[75] Inventors: John Oakes, Winsford; David W. Thornthwaite, Neston, both of Great Britain

[73] Assignee: Lever Brothers Company, Division of Conopco, Inc., New York, N.Y.

[21] Appl. No.: 705,453

[22] Filed: May 24, 1991

[30] Foreign Application Priority Data

May 24, 1990 [GB] United Kingdom ............... 9011618

[51] Int. Cl.$^5$ .................... C09K 3/00; C11D 3/395
[52] U.S. Cl. .................... 252/186.38; 252/186.39; 252/95; 558/452; 558/455
[58] Field of Search ............ 252/186.38, 186.39, 252/95; 558/452, 455

[56] References Cited

U.S. PATENT DOCUMENTS

| | | | |
|---|---|---|---|
| 3,986,973 | 10/1976 | Loffelman et al. | 252/102 |
| 4,551,526 | 11/1985 | Mai et al. | 558/452 |
| 4,559,158 | 12/1985 | Hase et al. | 252/102 |
| 4,915,863 | 4/1990 | Aoyagi et al. | 252/102 |
| 4,978,770 | 12/1990 | Aoyagi et al. | 558/455 X |

FOREIGN PATENT DOCUMENTS

| | | | |
|---|---|---|---|
| 599168 | 5/1960 | Canada | 558/452 |
| 49577 | 4/1982 | European Pat. Off. | |
| 303520 | 2/1989 | European Pat. Off. | |
| 1-090296 | 9/1987 | Japan . | |
| 2-084499 | 9/1988 | Japan . | |
| 2-132196 | 11/1988 | Japan . | |

Primary Examiner—Richard D. Lovering
Assistant Examiner—Joseph D. Anthony
Attorney, Agent, or Firm—Milton L. Honig

[57] ABSTRACT

Bleaching compositions are disclosed comprising a peroxide bleaching agent and a novel cationic peroxyacid bleach precursor having at least one of the following groups (A) and (B):

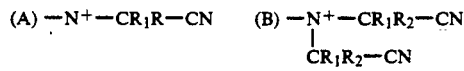

wherein $R_1$ and $R_2$ are each individually H, or a substituent group containing at least one carbon atom, provided that $R_1$ and $R_2$ are not both H.

The novel bleach precursor of the cationic nitrile type shows no tendency to deliquesce under normal atmospheric conditions.

14 Claims, No Drawings

BLEACHING COMPOSITION

FIELD OF THE INVENTION

This invention relates to an improved bleach composition, a novel cationic peroxyacid bleach precursor and a bleaching (detergent) composition containing said cationic peroxyacid bleach precursor.

THE RELATED ART

It is known that the bleach activity of hydrogen peroxide bleach compounds, such as the perborates, percarbonates, persilicates and perphosphates, can be improved so as to become effective at lower wash temperatures, i.e. at or below 60° C., by the use of peroxyacid bleach precursors, often also referred to as bleach activators.

Numerous substances have been disclosed and proposed in the art as usable peroxyacid bleach precursors. Conventionally, these precursors are reactive organic compounds having an O-acyl or N-acyl group, such as carboxylic acid esters, that in alkaline solutions containing a source of hydrogen peroxide will generate the corresponding peroxyacids, a reaction which is also referred to as perhydrolysis. They can be represented by the following general formula:

wherein R can be any suitable radical forming the RCO (acyl) radical and L is a suitable leaving group. It is believed that the reaction with hydrogen peroxide proceeds as follows:

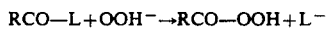

A leaving group is thus any group that is displaced from the peroxyacid bleach precursor as a consequence of nucleophilic attack on the precursor by the hydroperoxide anion. This, i.e. the perhydrolysis reaction, results in the formation of the peroxyacid. Generally, for a group to be a suitable leaving group, it must exert an electron-attracting effect, which facilitates expulsion of the leaving group from the tetrahydral intermediate formed by nucleophilic attack by the hydroperoxide anion. Many and diverse leaving group structures have been described in the patent literature (see, for example, EP-A-0120591). Not only do leaving groups add extra weight to bleach precursors of the conventional type but, once expelled from the precursor as a consequence of nucleophilic attack, they will remain as substantially useless by-products in the bleach solution.

Examples of the most representative precursors of this broad class include N,N,N',N'-tetraacetyl ethylene diamine (TAED), glucose pentaacetate (GPA), xylose tetraacetate (TAX), sodium-4-benzoyloxy benzene sulphonate (SBOBS), sodiumtrimethyl hexanoyloxy benzene sulphonate (STHOBS), tetraacetyl glucoluril (TAGU), tetraacetyl cyanuric acid (TACA), di-N-acetyldimethyl glyoxine (ADMG) and 1-phenyl-3-acetylhydantoin (PAH)—see, for example, GB-A-836,988; GB-A-907,356; EP-A-0098129 and EP-A-0120591, which represent only a small part of the large amount of patent literature disclosing precursors.

Recently, cationic peroxyacid precursors have attracted interest of Research workers as substantive and highly effective bleach activators. The same above-indicated general formula also applies to the general class of cationic peroxyacid precursors, but with the special feature of R being a radical containing a quaternary ammonium or quaternary phosphonium group, i.e.

wherein Q is N or P, preferably N.

Such cationic peroxyacid precursors are described in, for example, GB-A-1,382,594; U.S. Pat. No. 4,751,015; EP-A-0284292 and EP-A-0331229.

Cationic nitriles form a special class of cationic peroxyacid precursors. These compounds, which are described in EP-A-0303520, have at least one of the following groups (a) and (b):

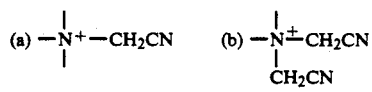

It is suggested here that the presence of the cationic group $\equiv N^+-CH_2CN$ is essential for the compound to exert its function as effective peroxyacid precursor. Apparently, the quaternary ammonium group activates the nitrile, not merely by an electron-withdrawing inductive effect, but by stabilization of the intermediate formed by nucleophilic attack by hydrogen peroxide on the carbon atom of the nitrile.

An advantage of these compounds is that they do not contain a leaving group as has routinely been the convention. It is believed that, upon perhydrolysis, they generate a peroxy imidic acid as the highly reactive bleaching species, without the loss of weight involved in having an attached leaving group, as illustrated in the following reaction:

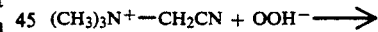

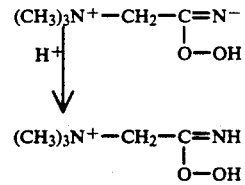

A serious drawback of the cationic nitriles of the art, however, is their highly hygroscopic nature. It has been observed that the above-described cationic nitriles of the art, e.g. $(CH_3)_3N^+-CH_2CN \ Cl^-$, take up water fairly quickly and deliquesce already upon exposure to an atmosphere of relative humidity of less than about 30% at ambient temperatures. Eventually they will hydrolyze and form the corresponding inactive amide, e.g.

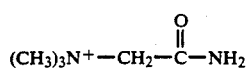

SUMMARY OF THE INVENTION

It has now surprisingly been found that it is possible to obtain an effective cationic peroxyacid precursor of the cationic nitrile type, which is, moreover, less hygroscopic in nature than the cationic nitriles of the art, thereby making it more suitable for practical use if at least one hydrogen atom on the α-carbon atom of the cationic nitrile group (a) or (b) is replaced by a substituent group containing at least one carbon atom.

One or both of said hydrogen atoms can be replaced by any substituent group ranging from the simplest methyl group to the most complex radical groups with increasing numbers of carbon atoms of any nature, including aliphatic, cyclic, alicyclic, aromatic, aryl and aralkyl groups with or without hetero-atoms. Only for practical reasons must the substitution not be such that the cationic nitrile becomes totally water-insoluble.

The novel cationic peroxyacid precursor of the invention can thus be defined as a compound having at least one of the following groups (A) and (B):

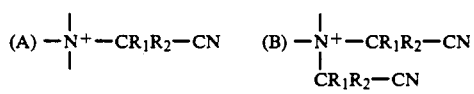

wherein $R_1$ and $R_2$ are each individually H, or a substituent group containing at least one carbon atom, provided that $R_1$ and $R_2$ are not both H.

Preferred compounds are those wherein the substituent group $R_1$ or $R_2$ is a straight or branched $C_1$-$C_8$ alkyl, alkenyl or alkyl ether; phenyl; $C_1$-$C_3$ alkylphenyl; or pyridyl group.

Compounds having at least one group (A) are furthermore preferred.

Accordingly, the invention provides a bleaching (detergent) composition comprising a peroxide bleach compound and a cationic peroxyacid precursor as defined hereinbefore and hereinafter.

Preferably, $R_1$ or $R_2$ is H, methyl or phenyl and the preferred compounds are those wherein:

1) $R_1$=H and $R_2$=methyl
2) $R_1$=methyl and $R_2$=methyl; and
3) $R_1$=H and $R_2$=phenyl such as for example:

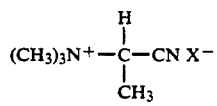     1)

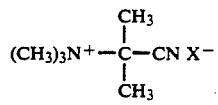     2)

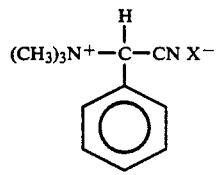     3)

wherein $X^-$ is a counter anion, such as $Cl^-$, $Br^-$ or $NO_3^-$.

Upon perhydrolysis, these compounds will yield the following quaternary ammonium-substituted peroxyimidic acids as the effective bleaching species:

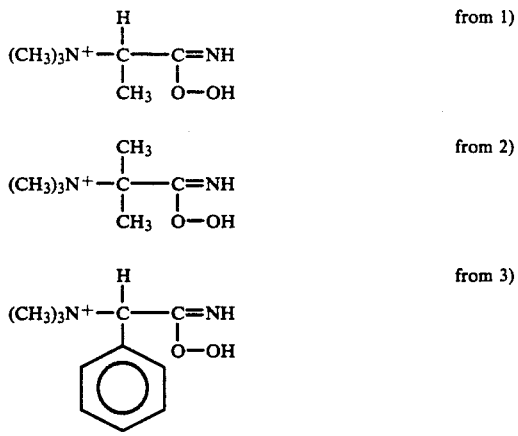

DETAILED DESCRIPTION

The compounds of the invention can be synthesized from fairly inexpensive raw materials. For instance, compound (3) can be prepared from benzaldehyde according to the following route:

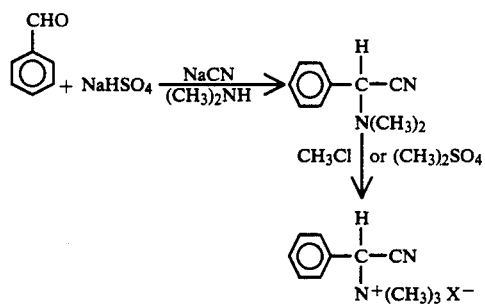

Thus, in general, the cationic peroxyacid precursor compounds of the invention can be prepared from alkyl or aromatic aldehydes or ketones. The aldehyde or ketone is reacted with sodium cyanide and a dialkylamine, e.g. dimethylamine in aqueous solution. This process gives good yields (abt. 90–95%) and has the potential for scale-up. The quaternization step is also straightforward, with good yields of about 95%.

A schematic diagram of the synthesis is given below:

R—CHO or $R_2$CO $H_2O$ | NaCN + $Me_2$NH

↓

R—CH—NMe$_2$ or R—C(R$^1$)—NMe$_2$
  |                    |
  CN                   CN $H_2O$ | $(CH_3)_2SO_4$ or $CH_3Cl$

↓

-continued

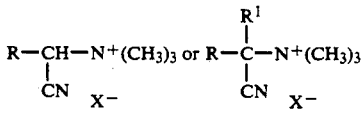

wherein X⁻ is CH₃SO₄⁻ or Cl⁻.

The cationic peroxyacid precursor compounds of the invention are thus compounds having the general formula:

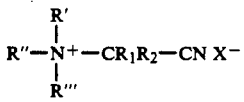

wherein $R_1$ and $R_2$ are as defined above; R' can be any suitable substituent including a straight or branched chain $C_1$-$C_{24}$ alkyl, alkenyl or alkaryl group or —$CR_1R_2$—CN; R″ and R‴ are each $C_1$-$C_4$ alkyl or hydroxyalkyl groups; or R″ can also be:

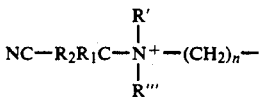

wherein n is an integer from 1 to about 4, forming compounds with two functional cationic groups connected via an alkylene bridging group.

Preferably, R' is $C_1$-$C_4$ alkyl, or a —$CR_1R_2$CN group, and R″ and R‴ are each $C_1$-$C_4$ alkyl, with particular preference for R'=methyl or —$CR_1R_2$CN, R″ is methyl and R‴ is methyl, thus forming cationic nitriles having either a trimethyl ammonium or a dimethyl ammonium group.

It is quite surprising that the mere addition of a substituent or substituents to the α-carbon atom can cause such a marked reduction in hygroscopicity and hydroscopicity, with substantially no tendency to deliquesce under normal atmospheric conditions.

Nor can it be expected that the novel branched cationic nitrile compounds of the invention are still as good peroxyacid bleach precursors as the nitriles of the art, generating peroxycarboxy imidic acid in very good yields.

Examination of the mechanism of the reaction between hydrogen peroxide and cationic nitriles has shown that, when cationic nitriles are added to alkaline solutions containing a source of hydrogen peroxide, various reactions are taking place which compete with each other, the rates of which will be dependent upon the reaction conditions.

Without wishing to be bound to any theory, it is believed that the formation of peroxycarboxy imidic acid (abbreviated as peroxy imidic acid), which is the active bleaching species, occurs almost instantaneously within a few seconds, followed by a relatively slower decay to the corresponding amide

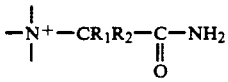

via hydrolysis or by mutual decomposition with hydrogen peroxide.

The cationic nitrile peroxyacid precursor of the invention can be effectively used with hydrogen peroxide or a hydrogen peroxide source in the form of a solid peroxide compound, such as sodium perborate and sodium percarbonate, in molar ratios of hydrogen peroxide to cationic nitrile of at least 1:1, at pH of at least 7.5 and already at a temperature of from about 10° C.

Advantageously, the cationic nitrile peroxyacid precursor of the invention is used in a bleaching composition with a peroxide bleach compound at molar ratios of peroxide to precursor from about 2:1 to about 20:1, preferably from 5:1 to 12:1, said bleaching composition having a 1-5 g/l solution pH of between 8 and 12, preferably from 8.5 to 10.5, and effective at a temperature of from about 20° C. to 60° C., preferably from 30° C. to 50° C.

Optimum bleaching performance is achieved at peroxide to precursor molar ratio of ≧5:1, at pH ≧9 and at a temperature of about 40° C.

Decrease of peroxide bleach level (i.e. at lower peroxide/precursor molar ratios) enhances hydrolytic instability, which is suppressed by increasing the peroxide level (i.e. increasing ratio peroxide to precursor). Below pH 9, yields of peroxyimidic acid decrease, owing to insufficient perhydrolysis and the maximum in bleach performance at 40° C. results from (excessive) increase of bleach instability at temperatures of above 40° C.

When the invention is applied to bleaching detergent compositions, the formulation, in addition to the essential peroxide compound and cationic nitrile bleach precursor, will usually contain a surface-active material, and desirably also detergency builders and other known ingredients commonly used in detergent compositions.

Peroxide bleach compounds usable in the present invention include the alkali metal peroxides, organic peroxides such as urea peroxide, and inorganic persalts, such as the alkali metal perborates, percarbonates, perphosphates, persilicates and persulphates. Mixtures of two or more such compounds may also be suitable. Particularly preferred are sodium perborate tetrahydrate and, especially, sodium perborate monohydrate. Sodium perborate monohydrate is preferred because it has excellent storage stability while also dissolving very quickly in aqueous solutions. Sodium percarbonate may be preferred for environmental reasons.

Alkylhydroperoxides are another suitable class of peroxygen compounds. Examples of these materials include cumene hydroperoxide and t-butyl hydroperoxide.

In such formulations the novel cationic nitrile peroxyacid precursor of the invention may be present at a level ranging from about 0.1% to 20% by weight, preferably from 0.5% to 10% by weight, particularly from 1% to 7.5% by weight, together with a peroxide bleaching compound, e.g. sodium perborate tetra- or monohydrate and sodium percarbonate, the amount of which is usually within the range of from about 2% to 40%, preferably from about 4% to 30%, particularly from about 10% to 25% by weight.

The surface-active material may be naturally derived, such as soap, or a synthetic material selected from anionic, nonionic, amphoteric, zwitterionic, cationic actives and mixtures thereof. Many suitable actives are commercially available and are fully described in literature, for example in "Surface Active Agents and Detergents", Volumes I and II, by Schwartz, Perry and Berch. The total level of the surface-active material may range up to 50% by weight, preferably being from about 1% to 40% by weight of the composition, most preferably 4 to 25%.

Synthetic anionic surface-actives are usually water-soluble alkali metal salts of organic sulphates and sulphonates having alkyl radicals containing from about 8 to about 22 carbon atoms, the term alkyl being used to include the alkyl portion of higher aryl radicals. Examples of suitable synthetic anionic detergent compounds are sodium and ammonium alkyl sulphates, especially those obtained by sulphating higher ($C_8$–$C_{18}$) alcohols produced, for example, from tallow or coconut oil; sodium and ammonium alkyl ($C_9$–$C_{20}$) benzene sulphonates, particularly sodium linear secondary alkyl ($C_{10}$–$C_{15}$) benzene sulphonates; sodium alkyl glyceryl ether sulphates, especially those esters of the higher alcohols derived from tallow or coconut oil and synthetic alcohols derived from petroleum; sodium coconut oil fatty acid monoglyceride sulphates and sulphonates; sodium and ammonium salts of sulphuric acid esters of higher ($C_9$–$C_{18}$) fatty alcohol alkylene oxide, particularly ethylene oxide, reaction products; the reaction products of fatty acids such as coconut fatty acids esterified with isethionic acid and neutralized with sodium hydroxide; sodium and ammonium salts of fatty acid amides of methyl taurine; alkane monosulphonates such as those derived by reacting alphaolefins ($C_8$–$C_{20}$) with sodium bisulphite and those derived by reacting paraffins with $SO_2$ and $Cl_2$ and then hydrolyzing with a base to produce a random sulphonate; sodium and ammonium $C_7$–$C_{12}$ dialkyl sulphosuccinates; and olefin sulphonates, which term is used to describe the material made by reacting olefins, particularly $C_{10}$–$C_{20}$ alpha-olefins, with $SO_3$ and then neutralizing and hydrolyzing the reaction product. The preferred anionic detergent compounds are sodium ($C_{11}$–$C_{15}$) alkylbenzene sulphonates, sodium ($C_{16}$–$C_{18}$) alkyl sulphates and sodium ($C_{16}$–$C_{18}$) alkyl ether sulphates.

Examples of suitable nonionic surface-active compounds which may be used, preferably together with the anionic surface-active compounds, include in particular the reaction products of alkylene oxides, usually ethylene oxide, with alkyl ($C_6$–$C_{22}$) phenols, generally 5–25 EO, i.e. 5–25 units of ethylene oxides per molecule; the condensation products of aliphatic ($C_8$–$C_{18}$) primary or secondary linear or branched alcohols with ethylene oxide, generally 6–30 EO, and products made by condensation of ethylene oxide with the reaction products of propylene oxide and ethylene diamine. Other so-called nonionic surface-actives include alkyl polyglycosides, long chain tertiary amine oxides, long chain tertiary phosphine oxides and dialkyl sulphoxides.

Amounts of amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

As stated above, soaps may also be incorporated in the compositions of the invention, preferably at a level of less than 25% by weight. They are particularly useful at low levels in binary (soap/anionic) or ternary mixtures together with nonionic or mixed synthetic anionic and nonionic compounds. Soaps which are used are preferably the sodium, or, less desirably, potassium salts of saturated or unsaturated $C_{10}$–$C_{24}$ fatty acids or mixtures thereof. The amount of such soaps can be varied between about 0.5% and about 25% by weight, with lower amounts of about 0.5% to about 5% being generally sufficient for lather control. Amounts of soap between about 2% and about 20%, especially between about 5% and about 10%, are used to give a beneficial effect on detergency. This is particularly valuable in compositions used in hard water when the soap acts as a supplementary builder.

The detergent compositions of the invention will normally also contain a detergency builder. Builder materials may be selected from 1) calcium sequestrant materials, 2) precipitating materials, 3) calcium ion-exchange materials and 4) mixtures thereof.

Examples of calcium sequestrant builder materials include alkali metal polyphosphates, such as sodium tripolyphosphate; nitrilotriacetic acid and its water-soluble salts; the akali metal salts of carboxymethyloxy succinic acid, ethylene diamine tetraacetic acid, oxydisuccinic acid, mellitic acid, benzene polycarboxylic acids, citric acid; and polyacetal carboxylates as disclosed in U.S. Pat. Nos. 4,144,226 and 4,146,495.

Examples of precipitating builder materials include sodium orthophosphate, sodium carbonate and long chain fatty acid soaps.

Examples of calcium ion-exchange builder materials include the various types of water-insoluble crystalline or amorphous aluminosilicates, of which zeolites are the best known representatives.

In particular, the compositions of the invention may contain any one of the organic or inorganic builder materials, such as sodium or potassium tripolyphosphate, sodium or potassium pyrophosphate, sodium or potassium orthophosphate, sodium carbonate, the sodium salt of nitrilotriacetic acid, sodium citrate, carboxymethyl malonate, carboxymethyloxy succinate and the water-insoluble crystalline or amorphous aluminosilicate builder materials, or mixtures thereof.

These builder materials may be present at a level of, for example, from 5 to 80% by weight, preferably from 10 to 60% by weight.

Apart from the components already mentioned, the detergent compositions of the invention can contain any of the conventional additives in the amounts in which such materials are normally employed in fabric washing detergent compositions. Examples of these additives include lather boosters, such as alkanolamides, particularly the monoethanol amides derived from palmkernel fatty acids and coconut fatty acids, lather depressants, such as alkyl phosphates and silicones, anti-redeposition agents, such as sodium carboxymethyl cellulose and alkyl or substituted alkyl cellulose ethers, other stabilizers, such as ethylene diamine tetraacetic acid, fabric softening agents, inorganic salts, such as sodium sulphate, and, usually present in very small amounts, fluorescent agents, perfumes, enzymes, such as proteases, cellulases, lipases and amylases, germicides and colourants.

The peroxyacid bleach precursors described herein are useful in a variety of cleaning products. These include laundry detergents, laundry bleaches, hard surface cleaners, toilet bowl cleaners, automatic dishwashing compositions and even denture cleaners. Precursors of the present invention can be introduced in a variety of product forms including powders, on sheets or other substrates, in pouches, in tablets or in non-aqueous liquids, such as liquid nonionic detergents.

Generally, for reasons of stability and handling, the bleach precursors will advantageously be presented in the form of particulate bodies comprising said bleach precursor and a binder or agglomerating agent. Many and diverse methods of preparing such precursor particulates have been described in various patent literature documents, such as e.g. in Canadian Patent No. 1,102,966; GB Patent No. 1,561,333; U.S. Pat. No. 4,087,369; EP-A-0,240,057; EP-A-0,241,962; EP-A-0,101,634 and EP-A-0,062,523. Each of these methods may be selected and applied to the bleach precursor of the invention.

Particulates incorporating the precursors of the present invention are normally added to the detergent base powder composition with the other dry-mix ingredients, such as enzymes, inorganic peroxygen bleaches and suds depressants. It will be appreciated, however, that the detergent base powder composition to which the precursor particulates are added may itself be made in a variety of ways, such as spray-drying, part-part processing, non-tower route processing, dry-mixing, agglomeration, granulation, extrusion, flaking etc., such ways being well known to those skilled in the art and not forming part of the present invention.

The peroxyacid precursors of the present invention can also be incorporated in detergent additive products. Such additive products are intended to supplement or boost the performance of conventional detergent compositions and may contain any of the components of such compositions, although they will not comprise all of the components present in a fully formulated detergent composition. Additive products in accordance with this aspect of the invention will normally be added to an aqueous liquor containing a source of (alkaline) hydrogen peroxide, although in certain circumstances a source of alkaline hydrogen peroxide may be included in the product.

Additive products in accordance with this aspect of the invention may comprise the compound alone in combination with a carrier, such as a compatible particulate substrate, a flexible non-particulate substrate or a container (e.g. pouch or sachet).

Examples of compatible particulate substrates include inert materials, such as clays and other aluminosilicates including zeolites both natural and synthetic of origin. Other compatible particulate carrier materials include hydratable inorganic salts, such as phosphates, carbonates and sulphates.

Additive products enclosed in bags or containers can be manufactured such that the containers prevent egress of their contents when dry but are adapted to release their contents on immersion in an aqueous solution.

In a further specific embodiment, the peroxyacid precursors of the invention are particularly suitable for incorporation in so-called non-aqueous liquid laundry detergent compositions together with a peroxide bleaching compound, e.g. sodium perborate, to impart an effective cleaning and stain-removing capacity to the products on fabrics and textiles.

Non-aqueous liquid detergent compositions including paste-like and gelatinous detergent compositions in which the precursor compounds can be incorporated are known from the art and various formulations have been proposed, e.g. in U.S. Pat. Nos. 2,864,770; 2,940,938; 4,772,412; 3,368,977; GB-A-1,205,711; 1,270,040; 1,292,352; 1,370,377; 2,194,536; DE-A-2,233,771; and EP-A-0,028,849.

These are compositions which normally comprise a non-aqueous liquid medium with or without a solid phase dispersed therein. The non-aqueous liquid medium may be a liquid surfactant, preferably a liquid nonionic surfactant; a non-polar liquid medium, e.g. liquid paraffin; a polar solvent, e.g. polyols, such as glycerol, sorbitol, ethylene glycol, optionally combined with low-molecular monohydric alcohols, e.g. ethanol or isopropanol; or mixtures thereof.

The solid phase can be builders, alkalis, abrasives, polymers, clays, other solid ionic surfactants, bleaches, fluorescent agents and other usual solid detergent ingredients.

The invention will be further illustrated in the following Examples.

EXAMPLE I

The following Example illustrates the preparation of several cationic nitrile peroxyacid precursor compounds according to the invention.

1) PREPARATION OF TERTIARY AMINO NITRILES (a) Dimethylaminopropionitrile

Sodium metabisulphite (38.0 g, 0.2 mole) and water (60 ml) were placed in a 250 ml RB 3-necked flask supplied with stirrer, swan-neck adaptor, pressure equalizing dropping funnel and condenser. Acetaldehyde (17.6 g, 0.4 mole) was added slowly to the stirred, cooled solution at such a rate that the temperature did not rise above 20° C. Potassium cyanide (26.52 g, 0.408 mole) was weighed out, in a fume cupboard, into a 100 ml beaker and water (40 ml) was added. The beaker was heated on a hotplate, with stirring, to aid dissolution. Once dissolved and cooled to room temperature, the solution was transferred to a 100 ml pressure equalizing dropping funnel. Dimethylamine (80 ml, 0.44 moles (25% aqueous solution)) was added over 25 minutes to the cooled bisulphite solution. Within one minute of the addition being complete, the potassium cyanide solution was added and the mixture stirred for 1 hour in an ice bath. It was then stirred for 2 hours at room temperature before extracting with ether (3×100 ml) and then back washing the combined ether fractions once with a little water. The ether was dried over sodium sulphate, filtered and evaporated to dryness at 40° C. The aqueous fractions were poured into bleach to destroy any residual potassium cyanide and all the glassware was soaked in bleach for 24 hours. A clear ether-soluble liquid was obtained (18.9 g, yield 96% $^1$H NMR ($\sigma$CDCl$_3$)) 1.4 (d, 3H, CH$_3$), 2.3 (s, 6H, N(CH$_3$)$_2$, 3.7 (q, 1H, CH) ppm.

(b) Dimethylamino butyronitrile

This material was prepared, using a method analogous to that used in 1(a), vide supra, except that propionaldehyde was used instead of acetaldehyde. The crude product was a liquid (23.34 g, yield 69%) and was purified by distillation to give 16.7 g, yield 50%, boiling point 142–153°·C., at atmospheric pressure. GLC 98.3% pure : $^1$H NMR ($\sigma$CDCl$_3$) 1.1 (t, rH, CH$_3$CH$_2$), 1.8 (m, 2H, CH$_3$CH$_2$), 2.3 (s, 6H, N(CH$_3$)$_2$, 3.4 (t, 1H, CH) ppm.

(c) Dimethylamine phenyl acetonitrile

This material was prepared, using a method analogous to that used in 1(a), vide supra, except that benzaldehyde was used instead of acetaldehyde. The ether soluble product (31.2 g, yield 97%) was vacuum-distilled at 76–78° C. at 0.8 mm Mg to give 28.4 g product (yield 89%: 'H NMR (σCDCl₃), 2.3 (s, 6H, (CH₃)₂N); 7.4 (m, 3H, ArH), 7.55 (d, 2H, ArH) ppm.

(d) Dimethylamine cyclohexane nitrile

This material was prepared, using a method analogous to that used in 1(a), vide supra, except that cyclohexanone was used instead of acetaldehyde. The potassium cyanide solution was added 30 seconds after the addition of the dimethylamine. The ether-soluble product (30.7 g, yield 100%), was vacuum-distilled to give 22.5 g product (yield 76%: 'H NMR (σCDCl₃) 1.3–2.2 (complex unresolved, 10H), 2.4 (5, 6h, (CH₃)₂N) ppm.

(e) N,N' dimethyl, NN' 2-propionitrile ethylene diamine

This material was prepared, using a method analogous to that used in 1(a), vide supra, except that NN' dimethyl ethylene diamine was used instead of dimethyl amine. The crude ether-soluble product (11.27 g, yield 58%) was vacuum-distilled at 130° C. and 1.0 mm Hg pressure to give 6.7 g product fractions (yield 34%: 'H NMR (σCDCl₃) 1.5 (d, 6H, CH₃—C), 2.3 (s, 6H, CH₃—N), 2.5-2.7 (m, 6H, N—CH₂CH₂N), 3.8 (m, 2H, CH) ppm.

(f) Methyl dimethylaminopropionitrile

Acetone cyanohydrin (17.0 g, 0.2 mole) was dissolved in water (30 ml) in a 250 ml 3-necked flask supplied with stirrer, condenser, pressure-equalizing dropping funnel, swan-neck adaptor and thermometer. Dimethylamine (40 ml, 0.22 mole (25% aqueous solution)) was added slowly, with cooling. The solution was stirred for 3 hours at room temperature and allowed to stand overnight before ether extraction (3×70 ml). The ether was dried over anhydrous sodium sulphate, filtered and evaporated to dryness at 35° C. to give 20.1 g product (yield 90%). 'H NMR (CDCl₃), 1.5 (s, 6H, C(CH₃)₂), 2.4 (b, 6H, N—(CH₃)₂) ppm.

(g) NN' dimethyl, NN' (α methylpropionitrile) ethylene diamine

This material was prepared, using a method analogous to that used in 1(f), vide supra, except that NN' dimethylene diamine was used instead of dimethylamine. A solid/gel separated out during the reaction, and the product was extracted with ether (600 ml) and brine. The ether-soluble solid was heated with hexane (250 ml), decanted off and the hexane cooled to 0° C. The solid crystallizing out was filtered off and vacuum-dried (11.9 g, yield 39.4%, 'H NMR (σCDCl₃), 1.5 (s, 12H, (CH₃)₂—C), 2.35 (s, 6H, CH₃N), 2.6 (s, 4H, N—CH₂CH₂N) ppm.

2) QUATERNISATION USING DIMETHYL SULPHATE

(i) 2-trimethylammonium 2-methyl propionitrile methosulphate

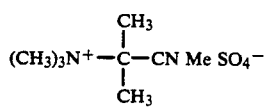

2-Dimethylamine 2-methyl propionitrile (6.32 g, 0.0564 mole) was dissolved in dry acetonitrile (50 ml) in a 250 ml 3-necked RB flask supplied with stirrer, condenser, pressure-equalizing dropping funnel and calcium chloride-drying tube. Neutral dimethyl sulphate (7.82 g, 0.062 mole (10% XS)) was dissolved in dry acetonitrile (20 ml) and added over 5 minutes, with stirring. After 20 minutes, the solution was heated to reflux for 5 hours before evaporating to dryness. Ether (100 ml) was added and the solid filtered off before vacuum-drying to give 12.78 g product (yield 95.2%). The ether-soluble fraction was evaporated to dryness and the residue destroyed by the addition of a neutralizing solution of NaOH/H₂O/meths. 'H NMR assay (D₂O, trioxan), 95.7% (σD₂O), 2.0 (s, 6H, C—(CH₃)₂ 3.35 (s, 9H (CH₃)₃N⁺), 3.75 (s, 3H, CH₃OSO₃⁻) ppm.

(ii) Phenyl trimethylammonium acetonitrile methosulphate

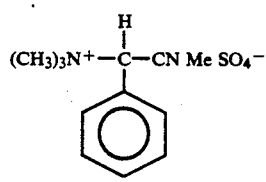

This material was prepared, using a method analogous to that used in 2(i), vide supra, except that phenyl dimethylamino acetonitrile was used instead of 2-dimethylamino 2-methyl propionitrile. A white solid (12.55 g, yield 88%) was obtained. 'H NMR assay (CDCl₃, trioxan), 94.4% (σCDCl₃) 3.45 (s, 9H, (CH₃)₃N⁺), 3.75 (s, 3H, CH₃OSO₃⁻), 6.6 (s, H, CH), 7.6 (m, 3H, ArH), 7.8 (d, 2H, ArH) ppm.

(iii) 1-Trimethyl ammonium cyclohexane nitrile methosulphate

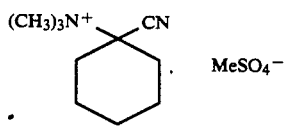

This material was prepared, using a method analogous to that used in 2(i), vide supra, except that dimethylamino cyclohexane nitrile was used instead of 2-dimethyl-2-methyl propionitrile. A yellow/white solid (6.0 g) was obtained. The yield data were not given because some product was lost due to bumping : 'H NMR (σD₂O), 3.4 (s, 9H (CH₃)₃N⁺), 3.75 (s, 3H, CH₃OSO₃⁻) ppm.

(iv) 2-Trimethyl ammonium propionitrile methosulphate

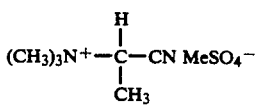

This material was prepared, using a method analogous to that used in 2(i), vide supra, except that 2-dimethylamino propionitrile was used instead of 2-dimethyl-2-methyl propionitrile. A brown oil (10.65 g, yield 93%) was obtained and this was further purified by crystallization from acetone to give white and white/brown crystals : 'H NMR (σD₂O), 1.9 (d, 3H, CH₃) 3.35 (s, 9H, (CH₃)₃N⁺, 3.75 (s, 3H, CH₃OSO₃⁻), 4.95 (g, 1H, CH) ppm Some of the methosulphate had hydrolyzed to bisulphite on crystallization.

(v) 2-Trimethyl ammonium butyronitrile methosulphate

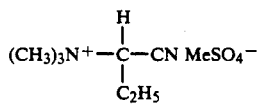

This material was prepared, using a method analogous to that used in 2(i), vide supra, except that 2-dimethylamino butyronitrile was used instead of 2-dimethyl-2-methyl propionitrile. A brown oil (17.93 g, yield 100%, water present) was obtained : 'H NMR ($\sigma D_2O$) 1.2 (t, 3H, $CH_3$—C), 2.2–2.4 (m, 2H, $CH_2$), 3.4 (s, 9H, $(CH_3)_3N^+$), 3.8 (s, 3H, $CH_3OSO_3^-$) 4.9 (t, 1H, CH) ppm.

EXAMPLE II

A branched nitrile of formula (1)

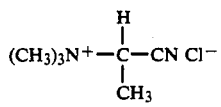

was used in a model experiment with sodium perborate at peroxide to nitrile molar ratio of 10:1, in a 30-minute isothermal wash at 40° C. and pH 10 using tea-stained test cloths.

The results obtained from repeated tests expressed as $\Delta R_{460}^*$ is 24–25 units, which are similar to the results of control experiments using the corresponding unbranched nitrile $(CH_3)_3 N^+$—$CH_2CN$ of the art.

When the experiments were repeated, using the nitrile compounds of formulae (2) and (3), similar bleaching results were obtained.

EXAMPLE III

This Example shows the influence of branching (substituents) of the α-carbon atom of cationic nitriles on the equilibrium-relative humidity (equilibrium RH).

Experiments were carried out with various cationic nitrile samples in closed jars at 28° C., in which the relative humidity can be adjusted and varied.

The equilibrium RH is the relative humidity of the headspace at which the sample commences to take up water and deliquesce.

| | Sample Compound | | Eq. RH (%) |
|---|---|---|---|
| (A) | $(CH_3)_3N^+$—$CH_2$—CN | $Cl^-$ | <30 |
| (B) | $C_8H_{17}(CH_3)_2N^+$—$CH_2$—CN | $Cl^-$ | <30 |
| (C) | $(C_2H_5)_3N^+$—$(CH_2)$—CN | $Cl^-$ | <30 |
| (1) | $(CH_3)_3N^+$—$CH(CH_3)$—CN | $Cl^-$ | 45 |
| (1') | $(CH_3)_3N^+$—$CH(CH_3)$—CN | $Br^-$/citrate$^-$ | 58/60 |
| (2) | $(CH_3)_3N^+$—$C(CH_3)_2$—CN | $Cl^-$ | 58 |

The above results clearly show that compounds (1), (1') and (2) of the invention are clearly superior to the compounds (A), (B) and (C) of the art.

What is claimed is:

1. A bleaching composition comprising a peroxide bleach compound present in an effective amount to bleach and a cationic peroxyacid precursor compound present in an effective amount to activate the peroxide bleach compound, the peroxyacid precursor compound having at least one of the following groups (A) and (B):

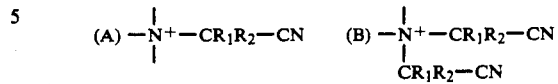

wherein $R_1$ and $R_2$ are each individually selected from the group consisting of H and a substituent group containing at least one carbon atom, provided that $R_1$ and $R_2$ are not both H.

2. A composition according to claim 1, wherein the substituent group is selected from the group consisting of $C_1$-$C_8$ alkyl; $C_1$-$C_8$ alkenyl; $C_1$-$C_8$ alkylether; phenyl; $C_1$-$C_3$ alkylphenyl; and pyridyl.

3. A composition according to claim 2, wherein at least one of $R_1$ and $R_2$ is selected from the group consisting of H, methyl and phenyl.

4. A composition according to claim 3, wherein $R_1$ is selected from the group consisting of H and methyl, and $R_2$ is methyl.

5. A composition according to claim 3, wherein $R_1$ is H and $R_2$ is phenyl.

6. A composition according to claim 1, wherein the cationic peroxyacid precursor has the general formula:

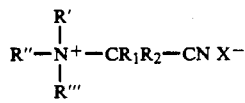

wherein R' is a substituent selected from the group consisting of $C_1$-$C_{24}$ alkyl, alkenyl and alkylether group; R" is selected from the group consisting of a $C_1$-$C_4$ alkyl and $C_1$-$C_4$ hydroxyalkyl and a radical having the formula:

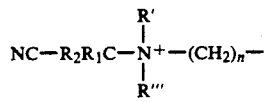

wherein n is an integer from 1 to about 4; R''' is a radical selected from the group consisting of $C_1$-$C_4$ alkyl and $C_1$-$C_4$ hydroxyalkyl groups; and $X^-$ is a counteranion.

7. A composition according to claim 6, wherein R', R" and R''' are $C_1$-$C_4$ alkyl groups.

8. A composition according to claim 7, wherein R', R" and R''' are methyl groups.

9. A composition according to claim 9, wherein the cationic peroxyacid precursor is a compound of formula :

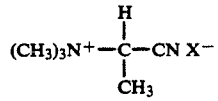

10. A composition according to claim 1, wherein the molar ratio of peroxide to precursor is from 2:1 to 20:1 and the composition has a 1–5 g/l solution pH of from 8 to 12.

11. A composition according to claim 10, Wherein said molar ratio is from 5:1 to 12:1 and said solution pH is from 8.5 to 10.5.

12. A composition according to claim 11, wherein the solution pH is ≧9.

13. A composition according to claim 10, wherein it further comprises a surface-active material at a level of up to 50% by weight.

14. A composition according to claim 13, which comprises:

(a) from 1 to 40% by weight of a surface-active material;
(b) from 5 to 80% by weight of a detergency builder;
(c) from 2 to 40% by weight of a peroxide bleach compound; and
(d) from 0.1 to 20% by weight of cationic peroxyacid precursor.

* * * * *